US006037327A

United States Patent [19]
Castillo et al.

[11] Patent Number: 6,037,327
[45] Date of Patent: Mar. 14, 2000

[54] SPECIFIC SACCHARIDE COMPOSITIONS AND METHODS FOR TREATING ALZHEIMER'S DISEASE AND OTHER AMYLOIDOSES

[75] Inventors: Gerardo Castillo, Seattle; Alan D. Snow, Lynnwood, both of Wash.

[73] Assignee: University of Washington, Seattle, Wash.

[21] Appl. No.: 09/141,628

[22] Filed: Aug. 28, 1998

Related U.S. Application Data

[60] Provisional application No. 60/057,144, Aug. 28, 1997.

[51] Int. Cl.[7] .................. A61K 31/70; A61K 31/095; C07H 3/02
[52] U.S. Cl. .................. 514/23; 514/53; 424/709; 536/122
[58] Field of Search .................. 514/23, 53; 424/78.35, 424/709; 536/1.11, 122

[56] References Cited

U.S. PATENT DOCUMENTS

| | | | |
|---|---|---|---|
| 4,912,093 | 3/1990 | Michaeli | 514/53 |
| 4,956,347 | 9/1990 | Ban et al. | 514/54 |
| 5,242,932 | 9/1993 | Gandy et al. | 514/313 |
| 5,388,574 | 2/1995 | Ingebrethsen | 125/203.17 |
| 5,643,562 | 7/1997 | Kisilevsky et al. | 424/78.31 |
| 5,723,589 | 3/1998 | Miljkovic et al. | 536/1.11 |
| 5,840,294 | 11/1998 | Kisilevsky et al. | 424/78.31 |

OTHER PUBLICATIONS

Snow et al. "Proteoglycans in the Pathogenesis of Alzheimer's Disease and Other Amyloidoses," Neurobiology of Aging, vol. 10, pp. 481–497, 1989.
Puchtler et al. "On the Binding of Congo Red by Amyloid," pp. 355–364, 1961(?). (publication information unknown).
Benson et al. "Serum Amyloid a Protein in Amyloidoses, Rheumatic, and Neoplastic Diseases," Arthritis and Rheumatism, vol. 22, No. 1, pp. 36–42, Jan. 1979.
Kamei et al. "Amyloidoses Associated with Juvenile Rheumatoid Arthritis," Acta Pathol. Jpn., vol. 32, No. 1, pp. 123–133, 1982.
McAdam et al. "Association of Amyloidosis with Erythema Nodosum Leprosum Reactions and Recurrent Neutrophil Leucocytosis in Leprosy," Lancet, pp. 572–575, Sep. 27, 1975.
Metaxas et al. "Familial Mediterranean Fever and Amyloidosis," Kidney International, vol. 20, pp. 676–685, 1981.
Harada et al. "Human Amyloid Protein: Chemical Variability and Homogeneity," Journal of Histochemistry and Cytochemistry, vol. 19, No. 1, pp. 1–15, 1971.
Johnson et al. "Islet Amyloid, Islet–Amyloid Polypeptide, and Diabetes Mellitus," New England Journal of Medicine, vol. 321, No. 8, pp. 513–518, Aug. 24, 1989.
Johnson et al. "Islet Amyloid Polypeptide: Mechanisms of Amyloidogenesis in the Pancreatic Islets and Potential Roles in Diabetes Mellitus," Laboratory Investigation, vol. 66, No. 5, pp. 522–535, 1992.

Gejyo et al. "A New Form of Amyloid Protein Associated with Chronic Hemodialysis was Identified as $\beta_2$–Microglobulin," Biochemical and Biophysical Research Communications, vol. 129, vol. 3, pp. 701–706, Jun. 28, 1985.
Gejyo et al. "$\beta_2$–Microglobulin: A New Form of Amyloid Protein Associated with Chronic Hemodialysis," Kidney International, vol. 30, pp. 385–390, 1986.
Skinner et al. "The Prealbumin Nature of the Amyloid Protein in Familial Amyloid Polyneuropathy (FAP)–Swedish Variety," Biochemical and Biophysical Research Communications, vol. 99, No. 4, 1316–1322, Apr. 30, 1981.
Saraiva et al. "Amyloid Fibril Protein in Familial Amyloidotic Polyneuropathy, Portuguese Type," J. Clinical Invest., vol. 74, pp. 104–119, Jul. 1984.
Saraiva et al. "Studies on Plasma Transthyretin (Prealbumin) in Familial Amyloidotic Polyneuropathy, Portuguese Type," J. Lab. Clin. Med., vol. 102, No. 4, pp. 590–603, Oct. 1983.
Tawara et al. "Amyloid Fibril Protein in Type I Familial Amyloidotic Polyneuropathy in Japanese," J. Lab. Clin Med., vol. 98, No. 6, pp. 811–822, Dec. 1981.
Barner et al. "Donepezil Use in Alzheimer Disease," Annals of Pharmacotherapy, vol. 32, pp. 70–77, Jan. 1998.
Glenner et al. "Alzheimer's Disease: Initial Report of the Purification and Characterization of a Novel Cerebrovascular Amyloid Protein," Biochemical and Biophysical Research Communications, vol. 120, No.2, pp. 885–890, May 16, 1984.
Masters et al. "Amyloid Plaque Core Protein in Alzheimer Disease and Down Syndrome," Proc. Natl. Acad. Sci. USA, vol. 82, pp. 4245–4249, Jun. 1985.
Who–Iuis Nomenclature Sub–Committee, "Nomenclature of Amyloid and Amyloidosis," Bulletin of the World Health Organization, vol. 71, No. 1, pp. 105–108, 1993.
Ponte et al. "A New A4 Amyloid mRNA Contains a Domain Homologous to Serine Proteinase Inhibitors," Nature, vol. 331, pp. 525–527, Feb. 11, 1988.
Tanzi et al. "Protease Inhibitor Domain Encoded by an Amyloid Protein Precursor mRNA Associated with Alzheimer's Disease," Nature, vol. 331, pp. 528–532, Feb. 11, 1988.
Grundke–Iqbal et al. "Abnormal Phosphorylation of the Microtubule–Associated Protein $\tau$ (tau) in Alzheimer Cytoskeletal Pathology," Proc. Natl. Acad. Sci USA, vol. 83, pp. 4913–4917, Jul. 1986.

(List continued on next page.)

*Primary Examiner*—Ralph Gitomer
*Assistant Examiner*—Marjorie A. Moran
*Attorney, Agent, or Firm*—Patrick M. Dwyer

[57] ABSTRACT

A pharmaceutical agent for treating an amyloid disease in a patient, wherein the pharmaceutical agent comprises a saccharide containing at least one substituted anionic group, or a pharmaceutically acceptable salt of the saccharide containing at least one substituted anionic group, and in preferred embodiments is a therapeutically effective amount of glucose pentasulfate. The agent is directed to amyloid diseases in general and to Alzheimer's disease in particular. The pharmaceutical agent may advantageously be combined with a pharmaceutically acceptable carrier, diluent or excipient.

4 Claims, 6 Drawing Sheets

OTHER PUBLICATIONS

Kosik et al. "Microtubule–Associated Protein Tau (τ) is a Major Antigenic Component of Paired Helical Filaments in Alzheimer Disease," Proc. Natl. Acad. Sci. USA, vol. 83, pp. 4044–4048, Jun. 1986.

Lee et al. "A68: A Major Subunit of Paired Helical Filaments and Derivatized Forms of Normal Tau," Science, vol. 251, pp. 675–678, Feb. 8, 1991.

Mandybur "Cerebral Amyloid Angiopathy: The Vascular Pathology and Complications," Journal of Neuropathology and Experimental Neurology, vol. 45, No. 1, pp. 79–90, Jan. 1986.

Pike et al. "Structure–Activity Analysis of β–Amyloid Peptides: Contribution of the β25–35 Region to Aggregation and Neurotoxicity," Journal of Neurochem., vol. 64, No. 1, pp. 253–265, 1995.

Pike et al. "In Vitro Aging of β–Amyloid Protein Causes Peptide Aggregation and Neurotoxicity," Brain Research, vol. 563, pp. 311–314, 1991.

Pardridge et al. "Amyloid Angiopathy of Alzheimer's Disease: Amino Acid Composition and Partial Sequence of a 4,200–Dalton Peptide Isolated from Cortical Microvessels," Journal of Neurochem., vol. 49, No. 5, pp. 1394–1401, 1987.

Harrigan et al. "Beta Amyloid is Neurotoxic in Hippocampal Slice Cultures," Neurobiology of Aging, vol. 16, No. 5, pp. 779–789, 1995.

Flood et al. "Amnestic effects in mice of four synthetic peptides homologous to amyloid β protein from patients with Alzheimer desease," Proc. Natl. Acad. Sci. USA, vol. 88, pp. 3363–3366, Apr. 1991.

Games et al. "Alzheimer–type neuropthology in transgenic mice overexpressing V717F β–amyloid precursor protein," Nature, vol. 373, Feb. 9, 1995.

Flood et al. "An Amyloid β–protein fragment, Aβ[12–28], equipotently impairs post–training memory processing when injected into different limbic system structures," Brain Research, vol. 663, pp. 271–276, 1994.

Murrell et al. "A Mutation in the Amyloid Precursor Protein Associated with Hereditary Alzheimer's Disease," Science, vol. 254, Oct. 4 1991.

Broeckhoven et al. "Amyloid β Protein Precursor Gene and Hereditary Cerebral Hemorrhage with Amyloidosis (Dutch)," Science, vol. 24, Jun. 1 1990.

Haass et al. "The Swedish mutation causes early–onset Alzheimer's disease by β–secretase cleavage within the secretory pathway," Nature Medicine, vol. 1, No. 12, Dec. 1995.

Hardy. "Framing β–amyloid," Nature, vol. 1, Jul. 1992.

Levine. "Thioflavine T interaction with amyloid β–sheet struvtures," Int. J. Exp. Clin. Invest., vol. 2, pp. 1–6, 1995.

Naiki. "Kinetic Analysis of Amyloid Fibril Polymerization In vitro," Laboratory Investigation, vol. 65, No. 1, p. 104, 1991.

Levine. "Thioflavine T interaction with synthetic Alzheimer's desease β–amyloid peptides: Detection of amyloid aggregation in solution," Protein Science, vol. 2, pp. 404–410, 1993.

Naiki. "First–Order Kinetic Model of Alzheimer's β–amyloid Fibril Extension In Vitro," Laboratory Investigation, vol. 74, No. 2, p. 374, 1996.

Bloemen et al. "Adhesion molecules: a mew target for immunoliposome–mediated drug delivery," FEBS Letters, vol. 357, pp. 140–144, 1995.

Ranade. "Drug Delivery Systems. 1. Site–Specific Drug Delivery Using Liposomes as Carriers," Journal of Clinical Pharmacology, vol. 29; pp. 685–694, 1989.

Gliatech, Inc. "Inhibition of Beta amyloid Binding to glycosaminoglycans for treatment of alzheimer's disease," WIPO International Publication No. WO 95/06477, Mar. 9 1995. (PCT/US94/09853, Filed Aug. 29 1994).

Mannose Pentasulfate, Potassium Salt
(PTI-07499; MW=771; $C_6H_7O_{21}S_5K_5$)

Glucose Pentasulfate, Potassium Salt
(PTI-48579; MW=771; $C_6H_7O_{21}S_5K_5$)

SPECIFIC SACCHARIDE COMPOSITIONS AND METHODS FOR TREATING ALZHEIMER'S DISEASE AND OTHER AMYLOIDOSES

This application claims priority to provisional application Ser. No. 60/057144 filed Aug. 28, 1997.

TECHNICAL FIELD

The invention relates to specific saccharide compositions and methods for treating Alzheimer's disease and other amyloidoses; more particularly, it relates to compositions and methods for therapeutic intervention in Alzheimer's disease and other amyloidoses involving the use of substituted anionic groups in mono and poly saccharides or pharmaceutically acceptable salts thereof

BACKGROUND OF THE INVENTION

Alzheimer's disease is characterized by the accumulation of a 39–43 amino acid peptide termed the beta-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence implicates amyloid as a major causative factor of Alzheimer's disease pathogenesis.

A variety of other human diseases also demonstrate amyloid deposition and usually involve systemic organs (i.e. organs or tissues lying outside the central nervous system), with the amyloid accumulation leading to organ dysfunction or failure. In Alzheimer's disease and "systemic" amyloid diseases, there is currently no cure or effective treatment, and the patient usually dies within 3 to 10 years from disease onset.

Much work in Alzheimer's disease has been accomplished, but little is conventually known about compounds or agents for therapeutic regimes to arrest amyloid formation, deposition, accumulation and/or persistence that occurs in Alzheimer's disease and other amyloidoses.

New compounds or agents for therapeutic regimes to arrest or reverse amyloid formation, deposition, accumulation and/or persistence that occurs in Alzheimer's disease and other amyloidoses are therefore desperately needed.

DISCLOSURE OF THE INVENTION

A primary object of the present invention is to establish new methods and compositions which are useful for the treatment of the amyloid diseases. The amyloid diseases include, but are not limited to, the amyloid associated with Alzheimer's disease, Down's syndrome and hereditary cerebral hemorrhage with amyloidosis of the Dutch type (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as $beta_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin).

The methods of the invention involve administering to a subject the therapeutic compound glucose pentasulfate, and pharmaceutically acceptable salts thereof, or derivatives thereof, which inhibit amyloid formation, deposition, accumulation and/or persistence, and/or which cause dissolution/disruption of pre-existing amyloid. Accordingly, the compositions and methods of the invention are useful for inhibiting amyloidosis in disorders in which amyloid deposition occurs. The methods of the invention can be used therapeutically to treat amyloidosis or can be used prophylactically in a subject susceptible to amyloidosis. The methods of the invention result, at least in part, in directly inhibiting or causing a reduction in the beta-pleated sheet secondary structure of specific amyloid proteins, such as, but not limited to, the beta-amyloid protein (Aβ) of Alzheimer's disease and the islet amyloid polypeptide (i.e. amylin) of type II diabetes.

"Derivatives", "related derivatives", "derivatives thereof" or "closely related compounds" of glucose pentasulfate for the purposes of this application shall include but are not limited to, glucose monosulfate, glucose disulfate, glucose trisulfate, glucose tetrasulfate, and glucose pentasulfate existing as a monosaccharide, disaccharide, trisaccharide, tetrasaccharide, pentasaccharide, hexasaccharide, heptasaccharide, hexasaccharide, nonasaccharide, decasaccharide or other polysaccharides of increasing length. In addition, "derivatives" of glucose pentasulfate, include but are not limited to, glucose pentasulfate, pharmaceutically acceptable salts thereof, and derivatives (referred to above) which have been substituted at sulfate-containing positions with other anionic group(s). Preferred substitutions include, but are not limited to, the replacement of sulfates with phosphates, phosphonates, carboxylates, sulphonates, and/or any ring compounds (i.e. alicyclic or heterocyclic groups) containing anionic groups. In addition, multiple anionic groups can be of the same structural group (i.e. all carboxylates) or, alternatively, a combination of different anionic groups can be used (i.e. carboxylates and phosphates).

An "anionic group" of a therapeutic compound of the invention is a negatively charged moiety. For purposes of the invention, the anionic group is negatively charged at physiological pH.

As used herein, the term "monosaccharide" are simple sugars usually of the formula $C_6H_{12}O_6$ that can be combined to form oligosaccharides or polysaccharides. Monosaccharide include enantiomers and both the D and L stereoisomers of monosaccharide. Carbohydrates, which include substituted and unsubstituted mono, oligo, and polysaccharides, can have multiple anionic groups attached to each monosaccharide moiety.

Another object of the present invention is to use the saccharide glucose pentasulfate and related derivatives for the treatment of amyloid formation, deposition, accumulation and/or persistence in Alzheimer's disease, type II diabetes and other amyloidoses. However, the glucose pentasulfate may exist as a monosaccharide, or as saccharides of increasing length (i.e. polysaccharides) such as, but not limited to, disaccharides, trisaccharides, tetrasaccharides, pentasaccharides, hexasaccharides, heptasaccharides, octasaccharides, nonasaccharides, or decasaccharides.

Another object of the present invention is to use glucose pentasulfate and related derivatives for the treatment of amyloid formation, deposition, accumulation and/or persistence in Alzheimer's disease, type II diabetes and other amyloidoses.

Another object of the present invention is to use commercially available, or to make commercially available, pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, and/or sterile packaged powders, which contain glucose pentasulfate or related derivatives to treat patients with Alzheimer's disease, type II diabetes and other amyloidoses.

Yet another object of the present invention is to use glucose pentasulfate or related derivatives as potent agents which inhibit amyloid formation, amyloid deposition, amyloid accumulation, amyloid persistence, amyloid-proteoglycan/glycosaminoglycan (PG/GAG) interactions, and/or cause a dissolution of pre-formed or pre-deposited amyloid fibrils in Alzheimer's disease, type II diabetes and other amyloidoses.

Yet another object of the present invention is to provide the use of glucose pentasulfate or related derivatives (regardless of commercial source) for inhibition of amyloid formation, deposition, accumulation, and/or persistence, regardless of its clinical setting.

Yet another object of the present invention is to provide compositions and methods involving administering to a subject a therapeutic dose of glucose pentasulfate or related derivatives which inhibit amyloid deposition. Accordingly, the compositions and methods of the invention are useful for inhibiting amyloidosis in disorders in which amyloid deposition occurs. The compounds of the invention can be used therapeutically to treat amyloidosis or can be used prophylactically in a subject susceptible to amyloidosis. The methods of the invention result, at least in part, in directly inhibiting amyloid fibril formation and/or causing dissolution of preformed amyloid fibrils. It is believed that glucose pentasulfate's mechanism of action works by directly inhibiting β-pleated sheet secondary structure folding of particular amyloid proteins (ie. with unique amino acid sequences), such as, but not limited to, the beta-amyloid protein (Aβ) of Alzheimer's disease and the islet amyloid polypeptide (i.e. amylin) of type II diabetes.

Yet another object of the present invention is to provide pharmaceutical compositions for treating amyloidosis. The pharmaceutical compositions include a therapeutic compound of the invention in an amount effective to inhibit amyloid deposition and a pharmaceutically acceptable vehicle.

Yet another object of the present invention is the use of any and all synthetic compounds to glucose pentasulfate or related derivatives for use as potent agents which inhibit amyloid formation, amyloid deposition, amyloid accumulation, amyloid persistence, amyloid-PG/GAG interactions, and/or cause a dissolution of pre-formed or pre-deposited amyloid fibrils in Alzheimer's disease, type II diabetes and other amyloidoses.

Yet another object of the present invention is to provide the use of glucose pentasulfate and/or derivatives thereof [(regardless of commercial source and regardless of final form for consumption by humans, i.e. pills, tablets, caplets, soft and hard gelatin capsules, lozenges, sacchets, vegicaps, liquid drops, elixers, suspensions, emulsions, solutions, syrups, tea bags, aerosols (as a solid or in a liquid medium), suppositories, sterile injectable solutions, and/or sterile packaged powders] for inhibition of amyloid formation, deposition, accumulation, and/or persistence, regardless of its clinical setting.

Yet another object of the present invention is the use of any and all natural compounds (i.e. plant, animal or mineral) to glucose pentasulfate or related derivatives for use as potent agents which inhibit amyloid formation, amyloid deposition, amyloid accumulation, amyloid persistence, amyloid-PG/GAG interactions, and/or cause a dissolution of pre-formed or pre-deposited amyloid fibrils in Alzheimer's disease, type II diabetes and other amyloidoses.

It is yet another object of the invention to meet any or all of the needs summarized above.

These and such other objects of the invention as will become evident from the disclosure below are met by the invention disclosed herein.

One aspect of the invention is a pharmaceutical agent for treating an amyloid disease in a patient, wherein the pharmaceutical agent comprises a therapeutically effective amount of a saccharide containing at least one substituted anionic group, or a pharmaceutically acceptable salt of the saccharide containing one or more substituted anionic groups. The agent may also advantageously include a pharmaceutically acceptable carrier, diluent or excipient. The saccharide is preferably a saccharide selected from the group consisting of all monosaccharides, disaccharides, trisaccharides, tetrasaccharides, pentasaccharides, hexasaccharides, heptasaccharides, octasaccharides, nonasaccharides, and decassacharides. A preferred embodiment of the saccharide is a monosaccharide, and more preferably the monosaccharide is glucose. The therapeutically effective amount preferably has an amyloid inhibitory activity or efficacy of 40% or greater.

The saccharide preferably contains at least one substituted anionic group selected from the group consisting of all sulfates, sulphonates, phosphates, phosphonates, carboxylates. A preferred substituted anionic group is sulfate.

The agent is preferably selected from the group consisting of glucose monosulfate, glucose disulfate, glucose trisulfate, glucose tetrasulfate, glucose pentasulfate, and more preferably is glucose pentasulfate, or a pharmaceutically acceptable salt thereof, such as a potassium salt.

The therapeutically effective amount of glucose pentasulfate may be obtained from any commercially available source, such as pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, or sterile packaged powders, or made available in such forms.

Another aspect of the invention is method of treating an amyloid disease in a patient, comprising the step of administering to the patient a therapeutically effective amount of glucose pentasulfate, a pharmaceutically acceptable salt thereof, or a related derivative thereof. The therapeutically effective amount of glucose pentasulfate is preferably administered orally, by aerosol spray, or in a parenterally injectable or infusible form.

The present invention pertains in particular to the identification and surprising discovery that the saccharide glucose pentasulfate acts as an impressive inhibitor of Alzheimer's disease amyloid formation, and as a potent agent which causes the dissolution of pre-formed amyloid fibrils containing the Alzheimer's disease beta-amyloid protein (Aβ), and to a lesser extent the amyloid fibrils of type II diabetes (i.e. islet amyloid polypeptide or amylin).

It has been found that commercially available glucose pentasulfate caused a marked inhibition of Aβ amyloid fibril formation as determined using a Thioflavin T fluorometry assay. In direct comparison, other compounds containing an identical number of sulfate groups (i.e. five) such as mannose pentasulfate, and other sugars and/or sulfated-containing compounds such as sucrose octasulfate, sucrose hexasulfate, sucrose heptasulfate, methyl alpha-D-mannopyranoside 2,3,4,6-tetrasulfate, and methyl alpha-D-glucopyranoside 2,3,4,6-tetrasulfate, were all ineffective inhibitors of Aβ amyloid fibril formation, indicating the specificity observed with glucose pentasulfate. The inhibition by glucose pentasulfate on Aβ amyloid fibril formation occurred in a dose-dependent manner. In addition, glucose pentasulfate was found to be a potent dissolving agent of pre-formed Alzheimer's Aβ amyloid fibrils, as determined using a Thioflavin T fluorometry assay. This latter effect occurred in a dose-dependent manner and within a 4 day incubation period. Glucose pentasulfate also caused a dissolution of fibrils containing islet amyloid polypeptide (i.e. amylin) by 1 week of incubation. Lastly, glucose pentasulfate was also effective in the inhibition of Aβ-PG/GAG interactions as determined using a solid phase binding immunoassay. The latter inhibition by glucose pentasulfate on Aβ-PG/GAG interactions also occurred in a dose-dependent manner.

It is believed that one possible mechanism of action for glucose pentasulfate is by directly inhibiting β-pleated sheet secondary structure folding of particular amyloid proteins (ie. with unique amino acid sequences), such as, but not limited to, the beta-amyloid protein (Aβ) of Alzheimer's disease. Glucose pentasulfate which was effective in all of the studies described above was derived from commercial available glucose pentasulfate in a water soluble form, making it easily adaptable for oral use in humans. A particular aspect of the present invention is the use of glucose pentasulfate (or related derivatives) (in a pill, tablet or liquid form) from commercial sources for the treatment of amyloidosis in Alzheimer's disease and other amyloidoses. Use of glucose pentasulfate is expected to be beneficial to human patients at all stages of Alzheimer's disease, due to glucose pentasulfate's inherent ability to inhibit Aβ amyloid fibril formation (early to mid-stage Alzheimer's disease), cause dissolution of preformed amyloid fibrils (mid to late stages of Alzheimer's disease) and inhibit amyloid-PG/GAG interactions (all stages of Alzheimer's disease).

These and other features and advantages of the present invention will become more fully apparent when the following detailed description of the invention is read in conjunction with the accompanying figures.

In other aspects of the invention, a pharmaceutical agent is disclosed for treating an amyloid disease in a patient, wherein the pharmaceutical agent comprises a therapeutically effective amount of glucose pentasulfate or derivatives thereof. The pharmaceutical agent preferably has a therapeutically effective amount of glucose pentasulfate or derivatives thereof in a dosage in the range of from about 5 to 10,000mg/kg of body weight of the patient, per day, and more preferably in the range of from about 5 to 500 mg/kg of body weight of the patient, per day.

The amyloid disease for treatment with the pharmaceutical agent is selected from the group consisting of the amyloid associated with Alzheimer's disease, Down's syndrome and hereditary cerebral hemorrhage with amyloidosis of the Dutch type (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta$_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin).

Active compounds are administered at a therapeutically effective dosage sufficient to inhibit amyloid formation, deposition, accumulation or persistence in a subject. A therapeutically effective dosage preferably inhibits amyloid formation, deposition, accumulation or persistence by at least 20%, more preferably by at least 40%, even more preferably by at least 60%, and still more preferably by at least 80% relative to untreated subjects.

BEST MODE OF CARRYING OUT THE INVENTION

Amyloid and Amyloidosis

Figure 1:
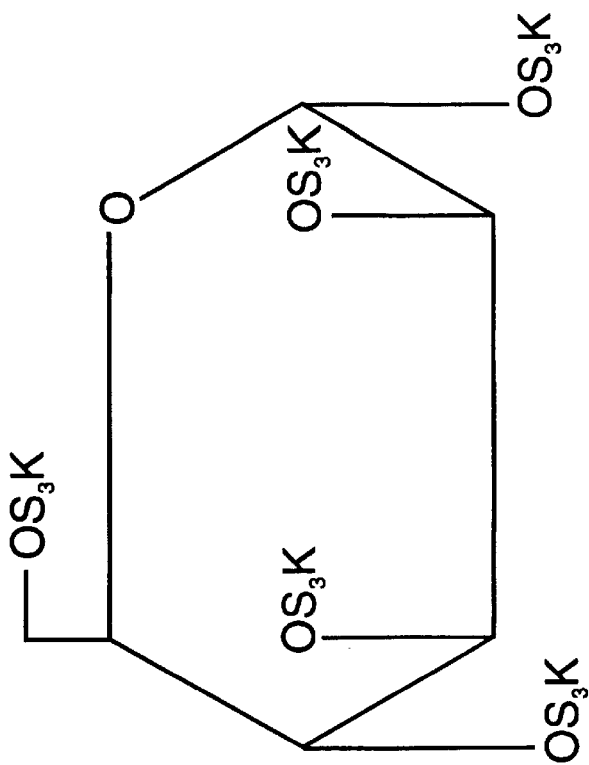
FIG. 1 depicts the chemical structure comparison of glucose pentasulfate (referred to as PTI-48579) versus mannose pentasulfate (referred to as PTI-07499). Glucose pentasulfate was found to be a potent inhibitor of Aβ amyloid fibril formation whereas mannose pentasulfate was not, even though both contained the same chemical formula and number of sulfate groups.
Figure 1:
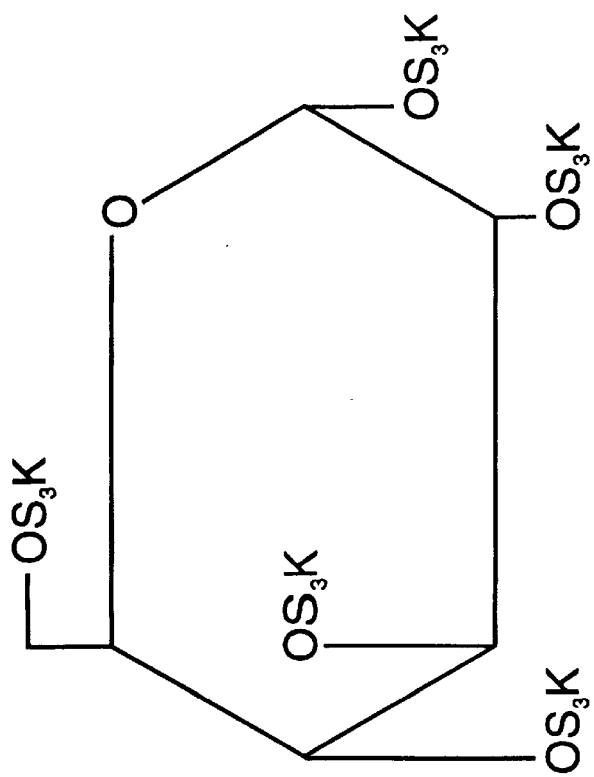

Amyloid is a generic term referring to a group of diverse, but specific extracellular protein deposits which all have common morphological properties, staining characteristics, and x-ray diffraction spectra. Regardless of the nature of the amyloid protein deposited all amyloids have the following characteristics: 1) an amorphous appearance at the light microscopic level and appear eosinophilic using hematoxylin and eosin stains; 2) all stain with Congo red and demonstrate a red/green birefringence as viewed under polarized light (Puchtler et al., *J. Histochem. Cytochem.* 10:355–364, 1962), 3) all contain a predominant beta-pleated sheet secondary structure, and 4) ultrastructurally amyloid usually consist of non-branching fibrils of indefinite length and with a diameter of 7–10 nm.

Amyloid today is classified according to the specific amyloid protein deposited. The amyloid diseases include, but are not limited to, the amyloid associated with Alzheimer's disease, Down's syndrome and Hereditary cerebral hemorrhage with amyloidosis of the Dutch type (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta$_2$microglobulin amyloid), the amyloid associated with senile cardiac amyloid and Familial Amyloidotic Polyneuropathy (wherein the specific amyloid is referred to as prealbumin or transthyretin amyloid), and the amyloid associated with endocrine tumors such as medullary carcinoma of the thyroid (wherein the specific amyloid is referred to as variants of procalcitonin).

Although amyloid deposits in clinical conditions share common physical properties relating to the presence of a beta-pleated sheet conformation, it is now clear that many different chemical types exist and additional ones are likely to be described in the future. It is currently thought that there are several common pathogenetic mechanisms that may be operating in amyloidosis in general. In many cases, a circulating precursor protein may result from overproduction of either intact or aberrant molecules (ex. plasma cell dyscrasias), reduced degradation or excretion (serum amyloid A in some secondary amyloid syndromes and beta$_2$-microglobulin in long-term hemodialysis), or genetic abnormalities associated with variant proteins (ex. familial amyloidotic polyneuropathy). Proteolysis of a larger protein precursor molecule occurs in many types of amyloidosis, resulting in the production of lower molecular weight fragments that polymerize and assume a beta-pleated sheet conformation as tissue deposits, usually in an extracellular location. What are the precise mechanisms involved, and the aberrant causes leading to changes in proteolytic processing and/or translational modifications is not known in most amyloids.

Systemic amyloids which include the amyloid associated with chronic inflammation, various forms of malignancy and Familial Mediterranean Fever (ie. AA amyloid or inflammation-associated amyloidosis)(Benson and Cohen, *Arth. Rheum.* 22:36–42, 1979; Kamei et al, *Acta Path. Jpn.* 32:123–133, 1982; McAdam et al, *Lancet* 2:572–573, 1975; Metaxas, *Kidney Int.* 20:676–685, 1981), and the amyloid associated with multiple myeloma and other B-cell dyscrasias (ie. AL amyloid)(Harada et al, *J. Histochem. Cytochem.* 19:1–15, 1971), as examples, are known to involve amyloid deposition in a variety of different organs and tissues generally lying outside the central nervous system. Amyloid deposition in these diseases may occur, for example, in liver, heart, spleen, gastrointestinal tract, kidney, skin, and/or lungs (Johnson et al, *N. Engl. J. Med.* 321:513–518, 1989). For most of these amyloidoses, there is no apparent cure or effective treatment and the consequences of amyloid deposition can be detrimental to the patient. For example, amyloid deposition in kidney may lead to renal failure, whereas amyloid deposition in heart may lead to heart failure. For these patients, amyloid accumulation in systemic organs leads to eventual death generally within 3–5 years. Other amyloidoses may affect a single organ or tissue such as observed with the Aβ amyloid deposits found in the brains of patients with Alzheimer's disease and Down's syndrome: the PrP amyloid deposits found in the brains of patients with Creutzfeldt-Jakob disease, Gerstmann-Straussler syndrome, and kuru; the islet amyloid (amylin) deposits found in the islets of Langerhans in the pancreas of 90% of patients with type II diabetes (Johnson et al, *N. Engl. J. Med.* 321:513–518, 1989; *Lab. Invest.* 66:522–535, 1992); the beta$_2$-microglobulin amyloid deposits in the medial nerve leading to carpal tunnel syndrome as observed in patients undergoing long-term hemodialysis (Geyjo et al, *Biochem. Biophys. Res. Comm.* 129:701–706, 1985; *Kidney Int.* 30:385–390, 1986); the prealbumin/transthyretin amyloid observed in the hearts of patients with senile cardiac amyloid; and the prealbuminin/transthyretin amyloid observed in peripheral nerves of patients who have Familial Amyloidotic Polyneuropathy (Skinner and Cohen, *Biochem. Biophys. Res. Comm.* 99:1326–1332, 1981; Saraiva et al, *J. Lab. Clin. Med.* 102:590–603, 1983; *J. Clin. Invest.* 74:104–119, 1984; Tawara et al, *J. Lab. Clin. Med.* 98:811–822, 1989).

Alzheimer's Disease and the Aging Population

Alzheimer's disease is a leading cause of dementia in the elderly, affecting 5–10% of the population over the age of 65 years (*A Guide to Understanding Alzheimer's Disease and Related Disorders*, edited by Jorm, New York University Press, New York, 1987). In Alzheimer's disease, the parts of the brain essential for cognitive processes such as memory, attention, language, and reasoning degenerate, robbing victims of much that makes us human, including independence. In some inherited forms of Alzheimer's disease, onset is in middle age, but more commonly, symptoms appear from the mid-60's onward. Alzheimer's disease today affects 4–5 million Americans, with slightly more than half of these people receiving care at home, while the others are in many different health care institutions. The prevalence of Alzheimer's disease and other dementias doubles every 5 years beyond the age of 65, and recent studies indicate that nearly 50% of all people age 85 and older have symptoms of Alzheimer's disease (1997 *Progress Report on Alzheimer's Disease*, National Institute on Aging/National Institute of Health). 13% (33 million people) of the total population of the United States are age 65 and older, and this % will climb to 20% by the year 2025 (1997 *Progress Report on Alzheimer's Disease*, National Institute on Aging/National Institute of Health).

Alzheimer's disease also puts a heavy economic burden on society as well. A recent study estimated that the cost of caring for one Alzheimer's disease patient with severe cognitive impairments at home or in a nursing home, is more than $47,000 per year (*A Guide to Understanding Alzheimer's Disease and Related Disorders*, edited by Jorm, New York University Press, New York, 1987). For a disease that can span from 2 to 20 years, the overall cost of Alzheimer's disease to families and to society is staggering. The annual economic toll of Alzheimer's disease in the United States in terms of health care expenses and lost wages of both patients and their caregivers is estimated at $80 to $100 billion (1997 *Progress Report on Alzheimer's Disease*, National Institute on Aging/National Institute of Health).

Tacrine hydrochloride ("Cognex"), the first FDA approved drug for Alzheimer's disease is a acetylcholinesterase inhibitor (Cutler and Sramek, *N. Engl. J. Med.* 328:808–810, 1993). However, this drug has showed limited success in the cognitive improvement in Alzheimer's disease patients and initially had major side effects such as liver toxicity. The second more recently FDA approved drug, donepezil (also known as "Aricept"), which is also an acetylcholinesterase inhibitor, is more effective than tacrine, by demonstrating slight cognitive improvement in Alzheimer's disease patients (Barner and Gray, *Ann. Pharmacotherapy* 32:70–77, 1998; Rogers and Friedhoff, *Eur. Neuropsych.* 8:67–75, 1998), but it does not appear to be a cure. Therefore, it is clear that there is a need for more effective treatments for Alzheimer's disease patients.

Amyloid as a Therapeutic Target for Alzheimer's Disease

Alzheimer's disease is characterized by the deposition and accumulation of a 39–43 amino acid peptide termed the beta-amyloid protein, Aβ or β/A4 (Glenner and Wong, *Biochem. Biophys. Res. Comm.* 120:885–890, 1984; Masters et al, *Proc. Natl. Acad. Sci. USA* 82:4245–4249, 1985; Husby et al, *Bull WHO* 71:105–108, 1993). Aβ is derived from larger precursor proteins termed beta-amyloid precursor proteins (or βPPs) of which there are several alternatively spliced variants. The most abundant forms of the βPPs include proteins consisting of 695, 751 and 770 amino acids (Tanzi et al, *Nature* 331:528–530, 1988; Kitaguchi et al, *Nature* 331:530–532, 1988; Ponte et al, *Nature* 331:525–527, 1988).

The small Aβ peptide is a major component which makes up the amyloid deposits of "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al, *Proc. Natl. Acad. Sci. USA* 83:4913–4917, 1986; Kosik et al, *Proc. Natl. Acad. Sci. USA* 83:4044–4048, 1986; Lee et al, *Science* 251:675–678, 1991). The pathological hallmarks of Alzheimer's disease is therefore the presence of "plaques" and "tangles", with amyloid being deposited in the central core of plaques. The other major type of lesion found in the Alzheimer's disease brain is the accumulation of amyloid in the walls of blood vessels, both within the brain parenchyma and in the walls of meningeal vessels which lie outside the brain. The amyloid deposits localized to the walls of blood vessels are referred to as cerebrovascular amyloid or congophilic angiopathy (Mandybur, *J. Neuropath. Exp. Neurol.* 45:79–90, 1986; Pardridge et al, *J. Neurochem.* 49:1394–1401, 1987).

For many years there has been an ongoing scientific debate as to the importance of "amyloid" in Alzheimer's disease and whether the "plaques" and "tangles" characteristic of this disease, were a cause or merely the consequences of the disease. Within the last few years, studies now indicate that amyloid is indeed a causative factor for Alzheimer's disease and should not be regarded as merely an innocent bystander. The Alzheimer's Aβ protein in cell culture has been shown to cause degeneration of nerve cells within short periods of time (Pike et al, *Br. Res.* 563:311–314, 1991; *J. Neurochem.* 64:253–265, 1995). Studies suggest that it is the fibrillar structure (consisting of a predominant β-pleated sheet secondary structure), characteristic of all amyloids, that is responsible for the neurotoxic effects. Aβ has also been found to be neurotoxic in slice cultures of hippocampus (Harrigan et al, *Neurobiol.Aging* 16:779–789, 1995) and induces nerve cell death in transgenic mice (Games et al, *Nature* 373:523–527, 1995; Hsiao et al, *Science* 274:99–102, 1996). Injection of the Alzheimer's Aβ into rat brain also causes memory impairment and neuronal dysfunction (Flood et al, *Proc. Natl. Acad. Sci.* 88:3363–3366, 1991; *Br. Res.* 663:271–276, 1994). Probably, the most convincing evidence that Aβ amyloid is directly involved in the pathogenesis of Alzheimer's disease comes from genetic studies. It has been discovered that the production of Aβ can result from mutations in the gene encoding, its precursor, beta-amyloid precursor protein (Van Broeckhoven et al, *Science* 248:1120–1122, 1990; Murrell et al, *Science* 254:97–99, 1991; Haass et al, *Nature Med.* 1:1291–1296, 1995). The identification of mutations in the beta-amyloid precursor protein gene which causes early onset familial Alzheimer's disease is the strongest argument that amyloid is central to the pathogenetic process underlying this disease. Four reported disease-causing mutations have now been discovered which demonstrate the importance of Aβ in causing familial Alzheimer's disease (reviewed in Hardy, *Nature Genet.* 1:233–234, 1992). All of these studies suggest that providing a drug to reduce, eliminate or prevent fibrillar Aβ formation, deposition, accumulation and/or persistence in the brains of human patients would serve as an effective therapeutic.

The present invention clearly demonstrates the effectiveness of glucose pentasulfate and derivatives thereof for the 1) inhibition of Alzheimer's Aβ amyloid fibril formation (important for patients in early to mid-stage Alzheimer's disease, 2) inhibition of Alzheimer's amyloid-PG/GAG interactions (important for patients in all stages of Alzheimer's disease), and 3) causing the dissolution/disruption of preformed Alzheimer's disease amyloid fibrils. In addition, the present invention demonstrates that glucose pentasulfate is effective in causing the dissolution/disruption of islet amyloid polypeptide (i.e. amylin) containing fibrils and therefore may serve as an effective treatment for ~90% of type II diabetic patients who have islet amyloid accumulation in the pancreas. Since the mechanism of action pertains to the disruption of β-pleated sheet structures which are part of all amyloids, regardless of the nature of the underlying amyloid protein involved or the clinical setting, the present invention of the use of glucose pentasulfate or derivatives thereof is anticipated to be useful for the treatment of all amyloid diseases as described herein.

11

Turning now to the drawings, the invention will be described in preferred embodiments.

EXAMPLES

The following examples are put forth so as to provide those with ordinary skill in the art with the disclosure and description of the identification and use of commercially available glucose pentasulfate or closely related derivatives to inhibit amyloid fibril formation, inhibit amyloid-PG/GAG interactions, and cause dissolution of preformed amyloid fibrils. However, it should not be construed that the invention is limited to these specific examples.

Example 1

Glucose Pentasultfate is a Potent Inhibitor of Alzheimer's Aβ (1–40) Amyloid Fibril Formation A previously described method of measuring amyloid fibril formation utilizing Thioflavin T fluorometry (H Naiki et al, *Lab. Invest.* 65:104–110, 1991; H Levine III, *Protein Sci.* 2:404–410, 1993; H Levine III, *Amyloid: Int. J. Exp. Clin. Invest.* 2:1–6, 1995; H Naiki and K. Nakakuki, *Lab. Invest.* 74:374–383, 1996) was employed initially to identify potential therapeutic compounds capable of inhibiting Aβ amyloid fibril formation. Using this sensitive assay, any decreases or increases in fluorescence were previously shown to correlate with a decrease or increase in the amount of amyloid fibrils (H Naiki et al, *Lab. Invest.* 65:104–110, 1991; H Levine III, *Protein Sci.* 2:404–410, 1993; H Levine III, *Amyloid: Int. J. Exp. Clin. Invest.* 2:1–6, 1995; H Naiki and K. Nakakuki, *Lab. Invest.* 74:374–383, 1996), allowing one to determine the identification and extent of potential inhibitors and/or enhancers of amyloid fibril formation.

In an initial set of studies, the effects of various compounds on Aβ (1–40) fibrillogenesis was assessed. For these initial studies, 25 μM of Aβ (1–40)(Bachem Inc., Torrance, Calif., USA; Lot #WM365) was incubated in microcentrifuge tubes at 37° C. for 1 week (in triplicate), either alone, or in the presence of 1.25 mM (ie. 1:50 M ratio of Aβ:test compound) of various commercially available compounds (described below) in 150 mM Tris HCl, 10 mM NaCl, pH 7.0 (TBS). The compounds tested included glucose pentasulfate (PTI-48579, potassium salt; molecular weight=771), mannose pentasulfate (PTI-07499, potassium salt; molecular weight=771), methyl alpha-D-glucopyranoside 2,3,4,6-tetrasulfate (PTI-20049, potassium salt; molecular weight=667), methyl alpha-D-mannopyranoside 2,3,4,6-tetrasulfate (PTI-20814, potassium salt; molecular weight=667), sucrose heptasulfate (PTI-70936, potassium salt; molecular weight=1169), sucrose hexasulfate (PTI-70946, potassium salt; molecular weight=1052), and sucrose octasulfate (PTI-70011, potassium salt; molecular weight=1288). The chemical structure comparison of glucose pentasulfate versus mannose pentasulfate is shown in FIG. 1.

To assess the effects of each compound on Aβ (1–40) fibril formation, 50 μl aliquots were taken from each tube for analysis at 1 hr, 1 day, 3 days, and 1 week. For each determination described above, following each incubation period, 50 μl of Aβ+/–test compounds were added to 1.2 ml of 100 μM Thioflavin T (Sigma Chemical Co., St. Louis, Mo.) in 50 mM NaPO$_4$ (pH 6.0). Initial studies indicated that increasing concentrations of Aβ gave a proportional increase in fluorescence in the presence of 100 μM Thioflavin T, ruling out the presence of any disproportionate inner filter effects in these studies. Fluorescence emission at 482 nm was measured on a Turner instrument-model 450 fluorometer at an excitation wavelength of 450 nm. For each determination, the fluorometer was calibrated by zeroing in the presence of the Thioflavin T reagent alone, and by seting the 50 ng/ml riboflavin (Sigma Chemical Co., St. Louis, Mo.) in the Thioflavin T reagent to 1800 fluorescence units. All fluorescence determinations were based on these references and any fluorescence given off by any of the compounds in the presence of the Thioflavin T reagent was always subtracted from all pertinent readings.

For all fibrillogenesis studies utilizing Thioflavin T fluorometry, comparisons of Aβ in the presence or absence of test compounds were based on paired Student's t tests with data shown as mean+/–standard deviation. Significance was reported at the 95% (p<0.05), 99% (p<0.01) and 99.9% (p<0.001) confidence levels.

Figure 2:
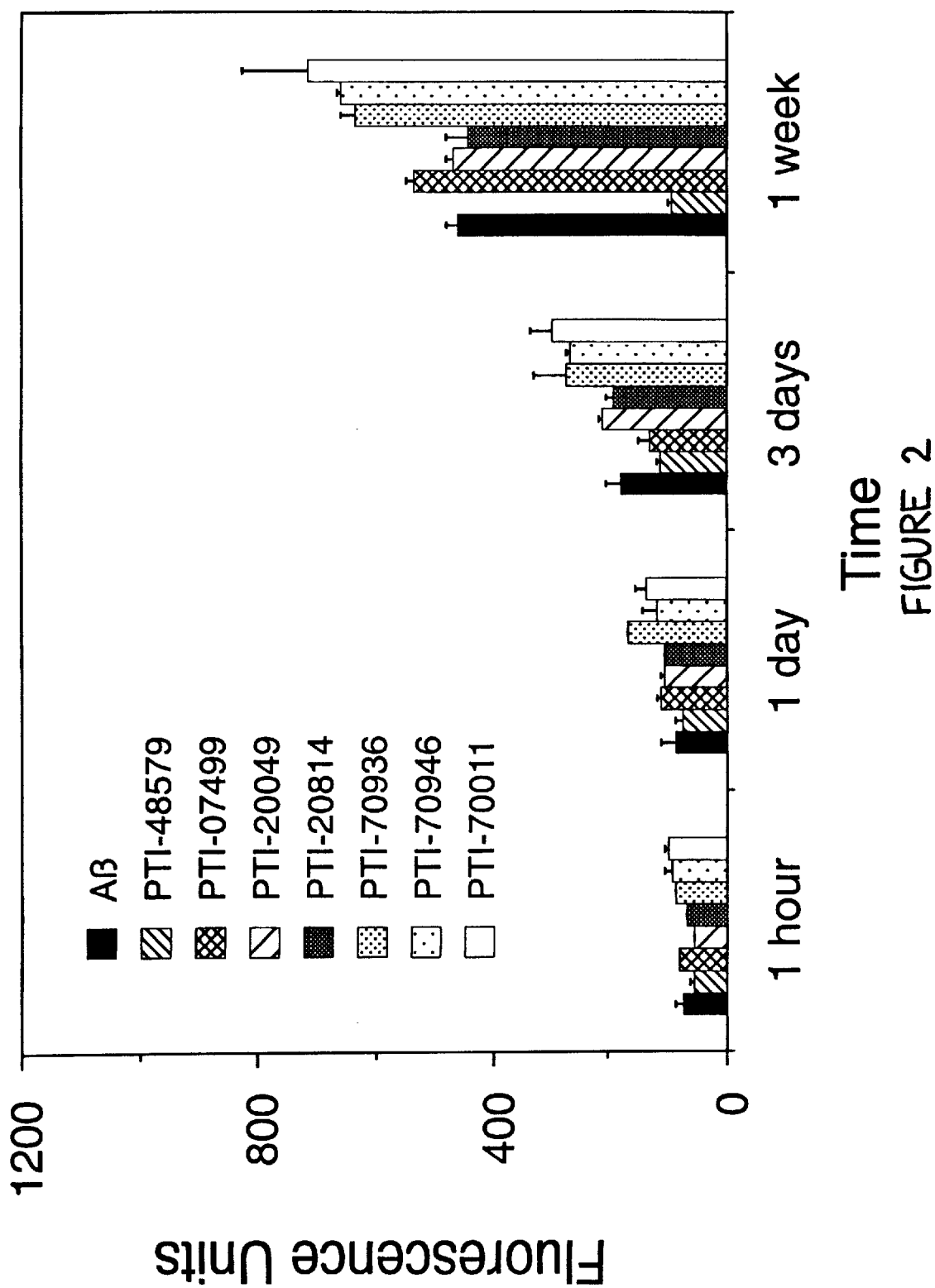
FIG. 2 is a black and white graph of a 1 week Thioflavin T fluorometry assay utilized to identify inhibitors of Aβ (1–40) amyloid fibril formation. Glucose pentasulfate (PTI-48579) is shown to be a potent inhibitor of Aβ (1–40) amyloid fibril formation at 3 and 7 days following incubation.

As shown in FIG. 2, in a first set of studies the effects of various test compounds on Aβ (1–40) amyloid fibril formation was evaluated over a 1-week incubation period. Freshly suspended Aβ (1–40) alone, following a 1-hour incubation at 37° C., demonstrated an initial fluorescence of 75+/–9 fluorescence units. During the 1-week incubation period, there was a gradual increase in the fluorescence of Aβ (1–40) alone, increasing 6.1-fold from 1 hour to 1 week, with a peak fluorescence of 459+/–18 fluorescence units observed at 1 week (FIG. 2). Only glucose pentasulfate (PTI-48579) inhibited Aβ (1–40) amyloid fibril formation. The significant inhibition of Aβ amyloid fibril formation by glucose pentasulfate was first observed at 3 days following incubation. Significant inhibition (p<0.001) by glucose pentasulfate (PTI-48579) on Aβ amyloid fibril formation was observed at 3 days and 1 week. By 1 week, glucose pentasulfate was effective in significantly (p<0.001) inhibiting amyloid fibril formation by 80%. This initial data indicated that glucose pentasulfate was specifically a potent inhibitor of Alzheimer's amyloid fibril formation. Note that mannose pentasulfate (PTI-07499) which consists of an identical chemical structure and molecular weight to that of glucose pentasulfate (i.e. $C_6H_7O_{21}S_5K_5$, molecular weight=771; see FIG. 1) did not inhibit Aβ (1–40) fibril formation. Since glucose pentasulfate and mannose pentasulfate both contain an identical number of sulfate groups (i.e.five), and only glucose pentasulfate was effective as an inhibitor of Alzheimer's amyloid fibril formation, this study implicated that aspects of the specific monosaccharide backbone of glucose played an important role in the mechanism of action.

Example 2

Figure 3:
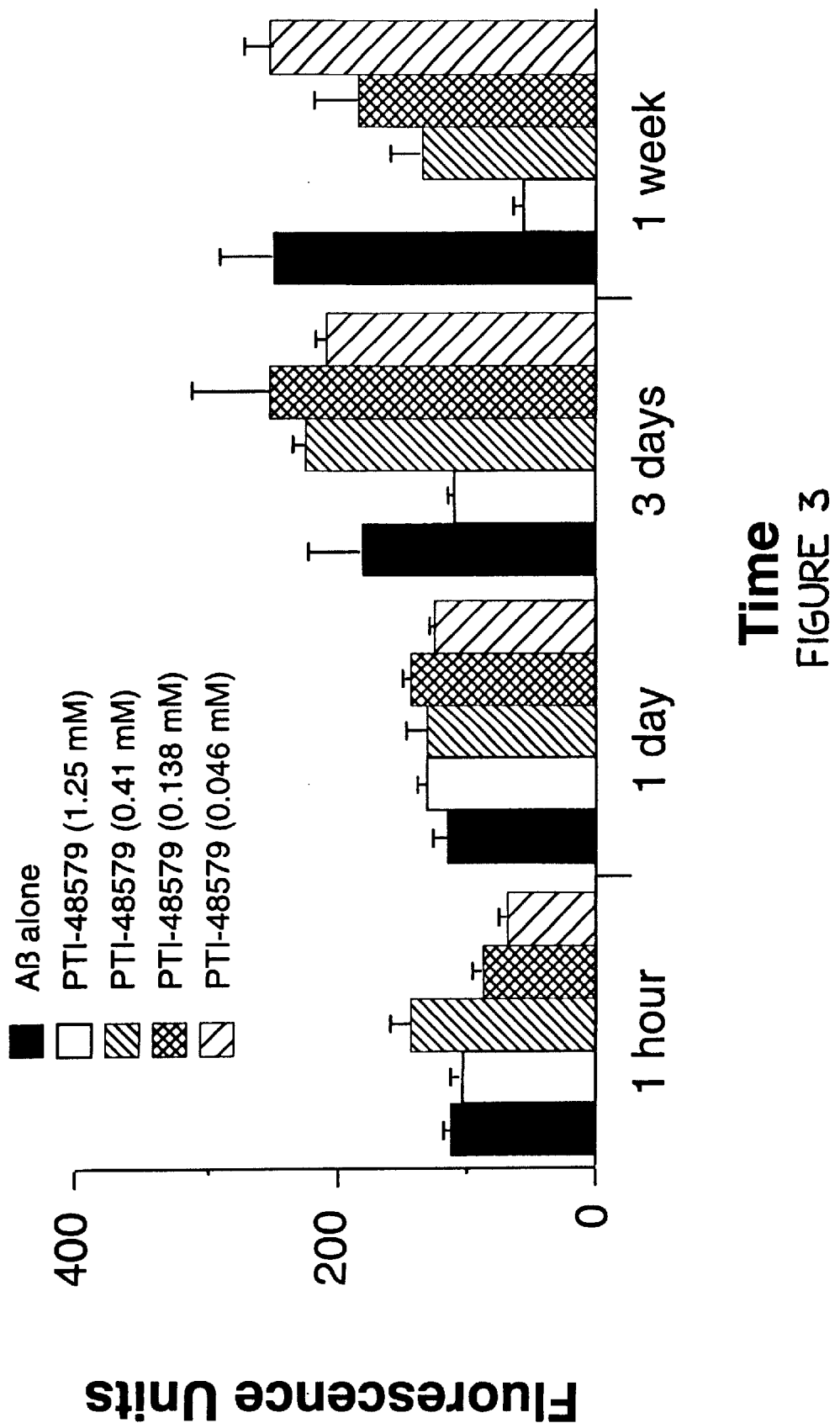
FIG. 3 is a black and white graph of a 1 week Thioflavin T fluorometry assay utilized to determine the potential dose-dependent effects of glucose pentasulfate (PTI-48579) on inhibition of Aβ amyloid fibril formation. Significant dose-dependent inhibition of Aβ (1–40) amyloid fibril formation is observed at 1 week of treatment with glucose pentasulfate.

Dose-Dependent Inhibition of Alzheimer's Aβ (1–40) Amyloid Fibril Formation by Glucose Pentasulfate In this study, the dose-dependent effects of glucose pentasulfate (PTI-48579) on Aβ (1–40) fibrillogenesis was determined using the Thioflavin T fluorometry assay. 25 μM of Aβ (1–40)(Bachem Inc., Torrance, Calif., USA; Lot #WM365) was incubated in microcentrifuge tubes at 37° C. for 1 week (in triplicate), either alone, or in the presence of 1.25 mM (ie. 1:50 M ratio of Aβ:PTI-48579), 0.41 mM, 0.138 mM and 0.046 mM of glucose pentasulfate in 150 mM Tris HCl, 10 mM NaCl, pH 7.0 (TBS). 50 μl aliquots were taken from each tube for analysis at 1 hr, 1 day, 3 days, and 1 week using Thioflavin T fluorometry as described in section 4.1. As shown in FIG. 3, freshly suspended Aβ (1–40) alone, following a 1-hour incubation at 37° C., demonstrated an initial fluorescence of 113+/–7 fluorescence units. During the 1-week incubation period, there was a gradual increase in the fluorescence of Aβ (1–40) alone, increasing 2.2-fold from 1 hour to 1 week, with a peak fluorescence of 250+/−50 fluorescence units observed at 1 week. Glucose pentasulfate (PTI-48579) caused a dose-dependent inhibition of Aβ amyloid fibril formation at 3 days and 1 week (FIG. 3). At 3 days, 0.046 mM, 0.138 mM and 0.41 mM of PTI-48579 did not significantly inhibit Aβ fibril formation, whereas 1.25 mM of PTI-48579 caused a significant (p<0.001) 39% inhibition of Aβ fibril formation. At 1 week a dose-dependent inhibition of Aβ (1–40) fibrillogenesis by glucose pentasulfate was observed. 1.25 mM and 0.41 mM of PTI-48579 caused a significant (p<0.001) 72% and 47% inhibition of Aβ (1–40) fibrillogenesis, respectively. This study therefore demonstrated that the effects of glucose pentasulfate on inhibition of Aβ (1–40) amyloid fibril formation occurred in a dose-dependent manner, particularly at 1 week postincubation.

Example 3

Glucose Pentasulfte Causes Dose-Dependent Dissolution of Pre-Formed Alzheimer's Disease Amyloid Fibrils The next study was implemented to determine whether glucose pentasulfate was capable of causing a dose-dependent dissolution/disruption of pre-formed Alzheimer's disease Aβ (1–40) amyloid fibrils. This type of activity would be important for any potential anti-amyloid drug which can be used in patients who already have substantial amyloid deposition in organs and/or tissues. For example, Alzheimer's disease patients in mid-to late stage disease have abundant amyloid deposits in their brains as part of both neuritic plaques and cerebrovascular amyloid deposits. A therapeutic agent capable of causing dissolution of pre-existing amyloid would be advantageous for use in these patients who are at latter stages of the disease process.

For this study, 1 mg of Aβ (1–40)(Bachem Inc., Torrance, Calif., USA; Lot #WM365) was dissolved in 1.0 ml of double distilled water (1 mg/ml solution) and then incubated at 37° C. for 1 week. 25 μM of fibrillized Aβ was then incubated at 37° C. in the presence or absence of glucose pentasulfate at concentrations of 1.25 mM, 0.63 mM, 0.31 mM and 0.16 mM containing 150 mM Tris HCl, 10 mM NaCl, pH 7.0. Following a 4 day incubation, 50 μl aliquots were added to 1.2 ml of 100 μM Thioflavin T (Sigma Chemical Co., St. Louis, Mo.) in 50 mM NaPO$_4$ (pH 6.0) for fluorometry readings as described in section 4.1.

Figure 4:
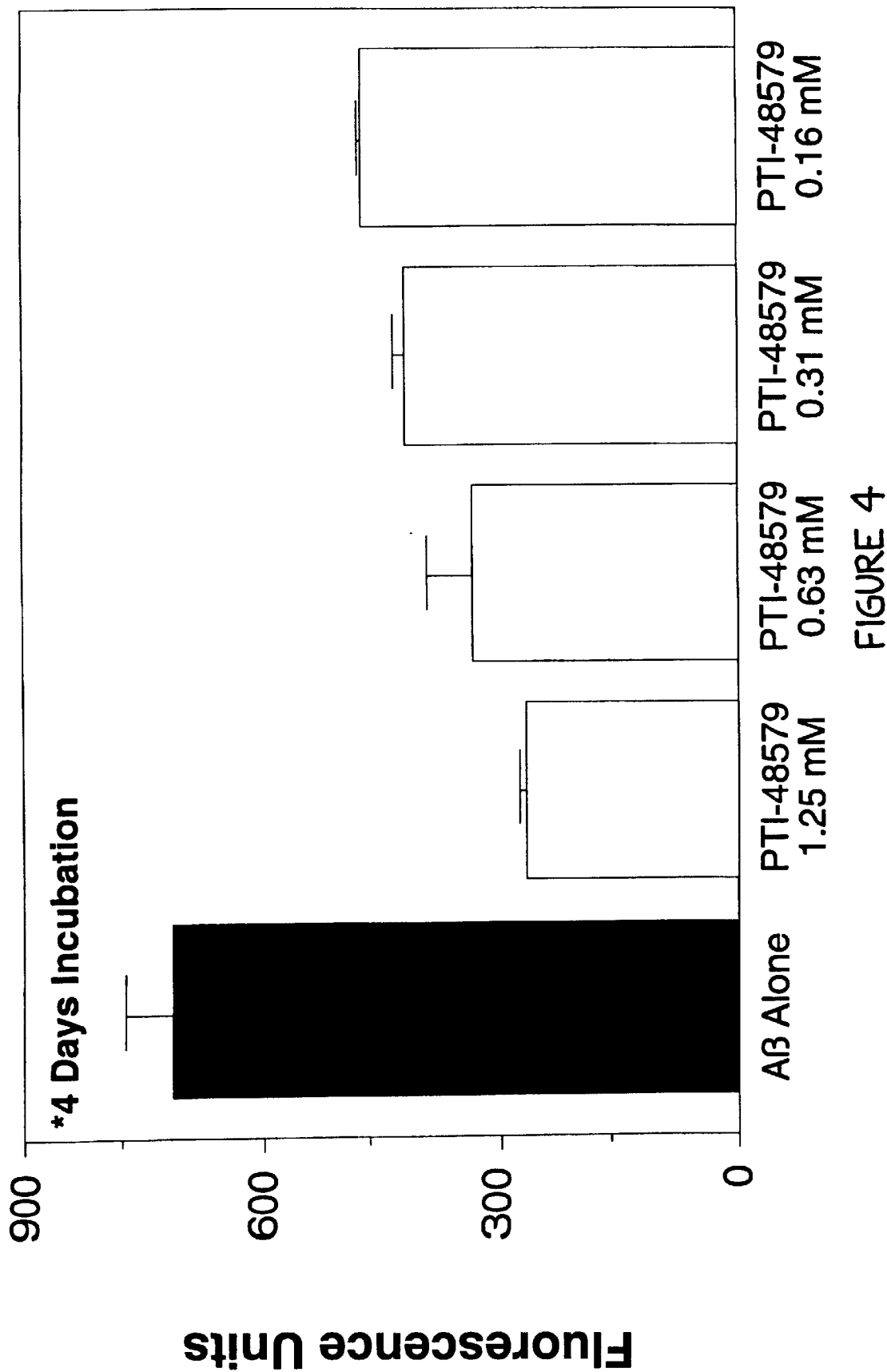
FIG. 4 is a black and white graph of a Thioflavin T fluorometry assay utilized to determine the potential dose-dependent effects of glucose pentasulfate (PTI-48579) on dissolution of pre-formed Aβ (1–40) amyloid fibrils within a 4 day incubation period. Glucose pentasulfate causes dissolution of pre-formed Aβ amyloid fibrils in a dose-dependent manner.

As shown in FIG. 4, dissolution/disruption of pre-formed Alzheimer's disease Aβ amyloid fibrils by glucose pentasulfate (PTI-48579) occurred in a dose-dependent manner. A significant (p<0.001) 60% dissolution of pre-formed Aβ amyloid fibrils was observed with 1.25 mM of PTI-48579, whereas 0.63 mM of PTI-48579 caused a significant (p<0.001) 47% dissolution. Furthermore, 0.31 mM and 0.16 mM of PTI-48579 still caused a significant (p<0.01) 31% and 23% dissolution of pre-formed Aβ amyloid fibrils. These data demonstrated that glucose pentasulfate causes dissolution/disruption of pre-formed Alzheimer's disease amyloid fibrils in a dose-dependent manner.

Example 4

Glucose Pentasulfate (PTI-48579) Inhibits Aβ Proteoglycan/Glycosaminoglycan Interactions in a Dose-Dependent Manner The next study was implemented to determine whether glucose pentasulfate was an effective inhibitor of Aβ-PG/GAG interactions, and whether this inhibition occurred in a dose-dependent manner. Since specific PGs/GAGs have been found to accumulate in amyloid deposits and are thought to prevent the body's natural ability to remove unwanted "amyloid" (reviewed in Snow and Wight, Neurobiology Aging 10:481–497, 1989), an inhibitor of Aβ-PG/GAG interactions should be a desirable additional target for an amyloid therapeutic. In this study a solid phase binding immunoassay was utilized to determine whether glucose pentasulfate was also an effective inhibitor of Aβ-PG/GAG interactions.

12 μg of heparin (molecular weight=5,000; obtained from the Sigma Chemical Company, St. Louis, Mo., USA) or heparan sulfate (molecular weight=~70,000; obtained from Seikagaku America, Rockville, Md.) in 80 μl of Tris-buffered saline containing 100 mM Tris-HCl, 50 mM NaCl, 3 mM NaN$_3$, pH 9.0 (TBS) was allowed to bind overnight at 4° C. to microtiter wells (Nunc plates, Maxisorb). The next day all of the microtiter wells were blocked for 2 hours by incubating with 300 μl of TBS with 0.05% Tween-20 (TTBS) plus 1% bovine serum albumin (BSA)(obtained from the Sigma Chemical Company, St. Louis, Mo., USA). Then, 100 μl of 5 μM Aβ 1–40(Bachem Inc., Torrance, Calif., USA; Lot #WM365) in TTBS containing 0.05% albumin in the presence or absence of glucose pentasulfate at concentrations of 2.5 mM, 0.83 mM, 0.28 mM and 0.093 mM were placed in wells (in triplicate) containing substrate bound perlecan or blank, and allowed to bind overnight at 4° C. The next day, the wells were rinsed once with TTBS, and then probed for 45 minutes with 100 μl of anti-6E10 (Senetek, Maryland Heights, Mo.)(which recognizes Aβ 1–17) diluted 1:1000 with TTBS. This was followed by rinsing once with TTBS and probed for 45 minutes with biotinylated goat-anti mouse (diluted 1:1000) containing streptavidin-peroxidase or anti-biotin-peroxidase (1:500 dilution of a 2 μg/ml solution)(Sigma Chemical Co., St. Louis, Mo.) in TTBS containing 0.1% BSA. The wells were then rinsed 3 times with TTBS and 100 μl of a substrate solution (OPD-Sigma Fast from Sigma Chemical Co., St. Louis, Mo.) was added to each well and allowed to develop for 5 minutes or until a significant color change was observed. The reaction was stopped with 50 μl of 4N H$_2$SO$_4$ and read on a Model 450 microplate reader (Biorad, Hercules, Calif., USA) at 490 nm.

Figure 5:
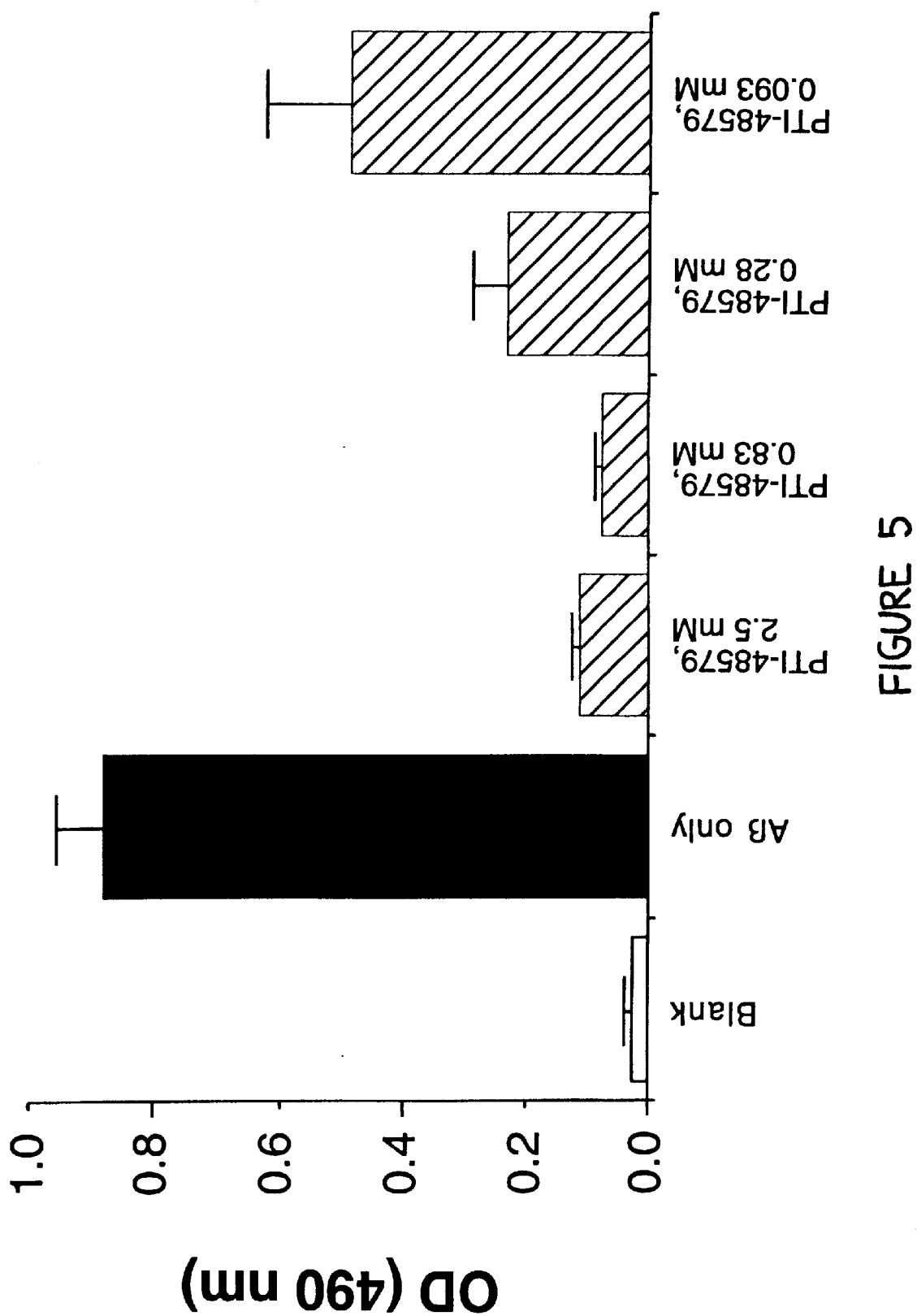
FIG. 5 is a black and white graph of a solid phase binding assay utilized to determine the potential dose-dependent effects of glucose pentasulfate (PTI-48579) on inhibition of Aβ-PG/GAG interactions. Significant dose-dependent inhibition of Aβ-heparan sulfate/heparin interactions is observed with treatment of glucose pentasulfate.

As shown in FIG. 5, glucose pentasulfate (PTI-48579) caused a significant (p<0.001) dose-dependent reduction in the binding of Aβ to substrate bound heparin. A significant (p<0.001) 78% inhibition was observed with 2.5 mM of PTI-48579, whereas 0.83 mM of PTI-48579 caused a significant (p<0.001) 92% inhibition (FIG. 5). 0.28 mM and 0.093 mM of PTI-48579 was still found to cause a significant inhibition of Aβ-heparin binding by 74% and 45%, respectively. PTI-48579 was similarly found to cause a significant dose-dependent inhibition of Aβ-heparan sulfate binding (not shown). These data demonstrated that glucose pentasulfate is also capable of inhibiting Aβ-PG/GAG interactions in a dose-dependent manner.

Example 5

Dissolution of Islet Amyloid Polypeptide Containing Fibrils by Glucose Pentasulfate but not by Mannose Pentasulfate 90% of patients with type II diabetes demonstrate the deposition and accumulation of amyloid fibrils in the islets of Langerhans in the pancreas. This amyloid is known as "islet amyloid" and consists of a 37 amino acid protein known as islet amyloid polypeptide or amylin. Islet amyloid is believed to contribute to the destruction of the beta-cells of the pancreas, thus eventually leading many patients to become insulin-dependent (ie. type I diabetes). Islet amyloid polypeptide has the uncanny ability to also form substantial amyloid fibrils immediately when placed in solution. The next study was therefore implemented to determine whether glucose pentasulfate also causes dissolution of another type of amyloidosis, and whether this effect was also long-lasting.

For this study, the method of Thioflavin T fluorometry as described above was used. Briefly, 25 $\mu$M of human islet amyloid polypeptide (Bachem Inc,Torrance, Calif., USA; Lot #WL934) was incubated in microcentrifuge tubes at 37° C. for 1 week (in triplicate), either alone, or in the presence of 1.25 mM glucose pentasulfate (PTI-48579; molecular weight=771) or mannose pentasulfate (PTI-07499; molecular weight=771). To assess the effects of glucose pentasulfate and mannose pentasulfate on islet amyloid polypeptide fibrillogenesis, 50 $\mu$l aliquots were taken from each tube for analysis at 1 hr, 1 day, 2 days, 3 days, 4 days and 1 week. For each determination described above, following each incubation period, 50 $\mu$l aliquots of islet amyloid polypeptide+/−glucose pentasulfate or mannose pentasulfate were added to 1.2 ml of 100 $\mu$M Thioflavin T (Sigma Chemical Co., St. Louis, Mo.) in 50 mM NaPO$_4$ (pH 6.0) for fluorometry readings as described in section 4.1.

Figure 6:
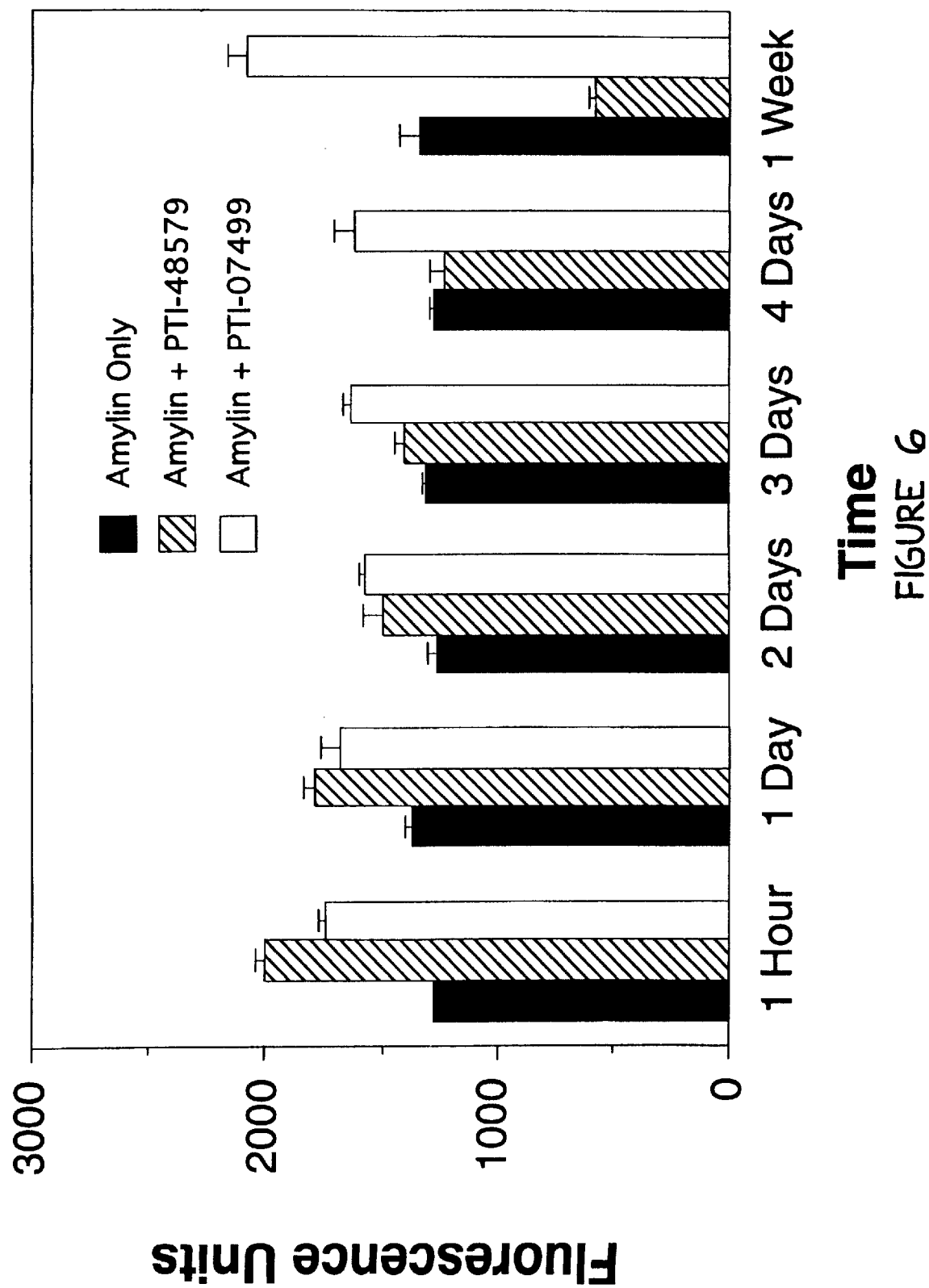
FIG. 6 is a black and white graph of a 1 week Thioflavin T fluorometry assay utilized to determine the effects of glucose pentasulfate (PTI-48579) and mannose pentasulfate (PTI-07499) on islet amyloid polypeptide (i.e. amylin) fibrillogenesis. Glucose pentasulfate caused a significant dissolution of islet amyloid polypeptide containing fibrils by 1 week of incubation, and only after an initial increase in islet amyloid polypeptide fibrillogenesis at earlier time points (i.e. 1 hour, 1 day and 2 days). On the other hand, mannose pentasulfate caused an increase in islet amyloid polypeptide fibrillogenesis at all time points.

As shown in FIG. 6, freshly suspended islet amyloid polypeptide alone, following a 1-hour incubation at 37° C., demonstrated an initial fluorescence of 1281+/−9 fluorescence units. During the 1 week incubation period, the levels of islet amyloid polypeptide containing fibrils as determined by Thioflavin T fluorescence stayed about the same (FIG. 6). Glucose pentasulfate (PTI-48579) was found to cause a significant dissolution of pre-formed amylin fibrils, only at 1 week by 57%. This apparent dissolution of islet amyloid polypeptide containing fibrils by glucose pentasulfate was only observed after an initial increase in islet amyloid polypeptide fibrillogenesis at earlier time points (i.e. 1 hour, 1 day and 2 days)(FIG. 6). On the other hand, mannose pentasulfate caused a significant increase in islet amyloid polypeptide fibrillogenesis at all time points (FIG. 6). This study therefore demonstrated that glucose pentasulfate, but not mannose pentasulfate, is also capable of causing significant dissolution of other forms of amyloid (such as islet amyloid polypeptide containing fibrils; important in type II diabetes), but only following prolonged periods of incubation (i.e. 1 week).

Further Aspects and Utilizations of the Invention
Therapeutic Applications

One embodiment of the present invention is to formulate prior to administration in a patient, a pharmaceutical formulation comprising glucose pentasulfate, pharmaceutically acceptable salts thereof, or related derivatives thereof, in one or more pharmaceutical acceptable carriers, diluents or excipients. In a preferred embodiment, a patient who has Alzheimer's disease or any other amyloid diseases, would orally consume glucose pentasulfate, pharmaceutically acceptable salts thereof, and/or related derivatives thereof, in pill, tablet, caplet, soft and hard gelatin capsule, lozenge, vegicap, liquid drop, solution, syrup, tea bag, and/or powder form.

In another preferred embodiment glucose pentasulfate, pharmaceutically acceptable salts thereof, or related derivatives thereof, obtained in any form could be further modulated using suitable carriers, excipients and diluents including lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweeting agents or flavoring agents. The compositions of the invention may be formulated so as to provide quick, sustained or delayed response of the active ingredient after administration to the patient. The compositions are preferably formulated in a unit dosage form, each dosage containing from about 5 to about 10,000 mg of glucose pentasulfate (or closely related derivatives), more usually about 400 to about 750 mg of glucose pentasulfate (or related derivatives). However, it will be understood that the therapeutic dosage administered will be determined by the physician in the light of the relevant circumstances including the clinical condition to be treated, the organ or tissues affected or suspected to be affected with amyloid accumulation, and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way. For each formulation provided as an example, lowering or raising of the glucose pentasulfate; a pharmaceutically acceptable salt thereof; or related derivatives thereof; concentration will cause a proportional lowering or raising of the other ingredients as indicated. Hard gelatin capsules may be prepared by using 500 mg of glucose pentasulfate, a pharmaceutically acceptable salt thereof (or its related derivatives), 400 mg of starch, and 20 mg of magnesium stearate. The above ingredients are mixed and filled into hard gelatin capsules in 920 mg quantities.

A tablet is prepared by using 500 mg of glucose pentasulfate, a pharmaceutically acceptable salt thereof, or related derivatives thereof, 800 mg of microcrystalline cellulose, 20 mg of fumed silicon dioxide and 10 mg of stearic acid. The components are blended and compressed to form tablets each weighing 1230 mg.

An aerosol solution is prepared by using 0.25 glucose pentasulfate, a pharmaceutically acceptable salt thereof, or related derivatives thereof, 29.75 ethanol, and 70 of propellent 22 (chlorodifluoromethane). The glucose pentasulfate, a pharmaceutically acceptable salt thereof, or related derivatives thereof, is mixed with ethanol. The mixture is added to a portion of the Propellent 22, cooled to −30° C., and transferred to a filling device. The required amount is then fed to a stainless steel container and diluted with the remainder of the propellent. The value units (listed above) are then fitted to the container. Such an aerosol form of glucose pentasulfate (or its related derivatives) may be useful for the treatment of amyloids involving the brain (such as Alzheimer's disease, Down's syndrome, prion diseases etc) by using an aerosol or nasal spray. Previous studies have suggested that in these central nervous system amyloidoses the initial form of entry of a possible environmental agent which may be playing a role in pathogenesis may be derived from the outside world through the nasal passages.

Tablets are made by using 120 mg of glucose pentasulfate, a pharmaceutically acceptable salt thereof, or related derivatives thereof, 90 mg of starch, 70 mg of microcrystalline cellulose, 8 mg of polyvinylpyrrolidone (as 10% in water), 9 mg of sodium carboxymethyl starch, 1 mg of magnesium stearate and 1 mg of talc (total=300 mg). Glucose pentasulfate, a pharmaceutically acceptable salt thereof, or related derivatives thereof, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 300 mg.

Capsules each containing 160 mg of medicant are made by using 160 mg of glucose pentasulfate, a pharmaceutically acceptable salt thereof, or related derivatives thereof, 118 mg of starch, 118 mg of microcrystalline cellulose, and 4 mg of magnesium stearate (total=400 mg). The glucose pentasulfate, a pharmaceutically acceptable salt thereof, or related derivatives thereof, cellulose, starch and magnesium stearate are blended, passed through a No. 45 mesh U.S. sieve, and filled into hard gelatin capsules in 400 mg quantities.

Suppositories each containing 225 mg of glucose pentasulfate, a pharmaceutically acceptable salt thereof, or related derivatives thereof, are made by using 225 mg of glucose pentasulfate, a pharmaceutically acceptable salt thereof, or related derivatives thereof, 2,000 mg of saturated fatty acid glycerides (total=2,225 mg). The glucose pentasulfate, a pharmaceutically acceptable salt thereof, or related derivatives thereof, are passed through a No. 60 mesh U.S. sieve and suspended in the saturated fatty acid glycerides previously melted using the minimum heat necessary. The mixture is then poured into a suppository mold of nominal 2 g capacity and allowed to cool.

Suspensions each containing 50 mg of medicant per 5 ml dose are made by using 50 mg of glucose pentasulfate, a pharmaceutically acceptable salt thereof, or related derivatives thereof, 50 mg of sodium carboxymethyl cellulose, 1.25 ml of syrup, 0.10 ml of benzoic acid solution, flavor, color, and purified water to total 5 ml. The medicant is passed though a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

An intravenous formulation is prepared by using 250 mg of glucose pentasulfate, a pharmaceutically acceptable salt thereof, or related derivatives thereof, and 1000 mg of isotonic saline. The solution of the above ingredients is administered intravenously at a rate of 1 ml per minute to a subject in need of treatment.

In a preferred embodiment the therapeutic compound of the invention can be administered in any pharmaceutically acceptable vehicle. As used herein "pharmaceutically acceptable vehicle" includes, but is not limited to, any and all solvents, sterile liquids, such as water and oils, including those of petroleum, animal, vegetable or synthetic origin, such as peanut oil, soybean oil, mineral oil, sesame oil and the like, dispersion media, coatings, antibacterial and antifungal agents, isotonic and adsorption delaying agents, and the like which are compatible with the activity of the compound and are physiologically acceptable to the subject. An example of a pharmaceutically acceptable vehicle is buffered normal saline (0.15 molar NaCl). The use of such media and agents for pharmaceutically active substances is well known in the art. Supplementary active compounds can also be incorporated into the compositions. Suitable pharmaceutical excipients include starch, glucose, lactose, sucrose, gelatin, malt, rice, fluor, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

In the methods of the invention, amyloid formation, deposition, accumulation and/or persistence in a subject is inhibited by administrating glucose pentasulfate, a pharmaceutically acceptable salt thereof, or related derivatives thereof, in a therapeutic dosage to the subject. The term subject is intended to include living organisms in which amyloidosis can occur. Examples of subjects include humans, monkeys, cows, dogs, sheep, cats, mice, rats, and transgenic species thereof. Administration of the compositions of the present invention to a subject to be treated can be carried out using known procedures, at dosages and for periods of time effective to inhibit amyloidosis in the subject. An effective amount of the therapeutic compound necessary to achieve a therapeutic effect may vary according to factors such as the amount of amyloid already deposited at the organ or tissue site in the subject, the age, sex and weight of the subject, and the ability of the therapeutic compound to inhibit amyloid formation, deposition, accumulation, persistence, and/or to cause dissolution of pre-formed amyloid in the subject. Dosage regimens can therefore be adjusted to provide the optimum therapeutic response. For example, several divided doses may be administered daily or the dose may be proportionally reduced as indicated by the needs of the therapeutic situation. A non-limiting example of an effective dose range for glucose pentasulfate, a pharmaceutically acceptable salt thereof, or related derivatives thereof, is between 5 and 500 mg/kg of body weight/per day.

Different modes of delivery of glucose pentasulfate, a pharmaceutically acceptable salt thereof, or related derivatives thereof, may be used. Accordingly, a preferred route of administration is oral administration. Alternatively, glucose pentasulfate, a pharmaceutically acceptable salt thereof, or related derivatives thereof, may be administered by other suitable routes such as subcutaneous, intravenous, intraperitoneal, all routes administered by injection. Depending on the route of administration, the active compound may be coated in a material to protect the compound from the action of acids and other natural conditions which may inactivate the compound.

To administer glucose pentasulfate, a pharmaceutically acceptable salt thereof, or related derivatives thereof, it may be necessary to coat the compound with, or co-administer the compound with, a material to prevent its activation. For example, the therapeutic compound may be administered to a subject in an appropriate carrier, for example, liposomes or a diluent. Pharmaceutically acceptable diluents include saline and aqueous buffer solutions. Liposomes include water-in-oil-in-water CGF emulsions as well as conventional liposomes.

The glucose pentasulfate, a pharmaceutically acceptable salt thereof, or related derivatives thereof, may also be administered parenterally or intraperitoneally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions or dispersions and sterile powders for the preparation of sterile injectable solutions or dispersion. In all cases, the composition must be sterile and must be fluid to the extent that easy use in the syringe exists. It must be stable under the conditions of manufacture and storage and must be preserved against the contaminating action of microorganisms such as bacteria and fungi. The vehicle can be a solvent or dispersion medium containing, for example, water, ethanol, polyol (for example glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, prabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the therapeutic agent plus any desired ingredients from a previously sterile-filtered solution thereof.

The glucose pentasulfate, a pharmaceutically acceptable salt thereof, or related derivatives thereof, for Alzheimer's disease and other central nervous system amyloidoses may be optimized to cross the blood-brain barrier. Methods of introductions include but are not limited to systemic administration, parenteral administration i.e., via an intraperitoneal, intravenous, perioral, subcutaneous, intramuscular, intraarterial, intradermal, intramuscular, intranasal, epidural and oral routes. In a preferred embodiment, glucose pentasulfate, a pharmaceutically acceptable (or its related derivatives) may be directly administered to the cerebrospinal fluid by intraventricular injection. In a specific embodiment, it may be desirable to administer glucose pentasulfate, a pharmaceutically acceptable salt thereof, or related derivatives thereof, locally to the area or tissue in need of treatment; this may be achieved by, for example, and not by way of limitation, local infusion during surgery, topical application, by injection, by infusion using a cannulae with osmotic pump, by means of a catheter, by means of a suppository, or by means of an implant.

In yet another embodiment glucose pentasulfate, a pharmaceutically acceptable salt thereof, or related derivatives thereof, may be delivered in a controlled release system, such as an osmotic pump. In yet another embodiment, a controlled release system can be placed in proximity to the therapeutic target, ie. the brain, thus requiring only a fraction of the systemic dose.

In yet another embodiment the therapeutic compounds of the invention can be formulated to cross the blood-brain-barrier, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs thus providing targeted drug delivery (see, e.g. Ranade, *J. Clin. Pharmacol.* 29:685, 1989). Exemplary targeting moieties include folate or biotin see, e.g. U.S. Pat. No. 5,416,016), mannosides (Umezawa et al, *Biochem. Biophys. Res. Comm.* 153, 1038, 1988), antibodies (Bloeman et al, *FEBS Lett* 357:140, 1995; Owais et al, *Antimicrob. Agents Chemother.* 39:180, 1995), surfactant protein A receptor (Briscoe et al, *Am. J. Physiol.* 1233:134, 1995), gp 120 (Schreier et al, *J. Biol. Chem.* 269:9090, 1994; Killion and Fidler, *Immunomethods* 4:273, 1994). In a preferred embodiment, the therapeutic compounds of the invention are formulated in liposomes.

With regard to systems and components above referred to, but not otherwise specified or described in detail herein, the workings and specifications of such systems and components and the manner in which they may be made or assembled or used, both cooperatively with each other and with the other elements of the invention described herein to effect the purposes herein disclosed, are all believed to be well within the knowledge of those skilled in the art. No concerted attempt to repeat here what is generally known to the artisan has therefore been made.

Industrial Applicability

Use of glucose pentasulfate, a pharmaceutically acceptable salt thereof, or derivatives thereof, is anticipated to benefit human patients with Alzheimer's disease and other amyloidoses due to glucose pentasulfate's newly discovered ability to inhibit amyloid fibril formation, inhibit amyloid-proteoglycan interactions, inhibit amyloid-glycosaminoglycan interactions, and cause dissolution and/or disruption of preformed amyloid fibrils.

In compliance with the statute, the invention has been described in language more or less specific as to structural features. It is to be understood, however, that the invention is not limited to the specific features shown, since the means and construction shown comprise preferred forms of putting the invention into effect. The invention is, therefore, claimed in any of its forms or modifications within the legitimate and valid scope of the appended claims, appropriately interpreted in accordance with the doctrine of equivalents.

We claim:

1. A method of treating an amyloid disease in a patient, comprising a step of administering to the patient a therapeutically effective amount of glucose pentasulfate, a pharmaceutically acceptable salt thereof, or a related derivative thereof.

2. The method of claim 1 wherein the therapeutically effective amount of glucose pentasulfate is administered orally.

3. The methods of claim 1 wherein the therapeutically effective amount of glucose pentasulfate is administered by aerosol spray.

4. The method of claim 1 wherein the therapeutically effective amount of glucose pentasulfate is administered in a parenterally injectable or infusible form.

* * * * *

UNITED STATES PATENT AND TRADEMARK OFFICE
CERTIFICATE OF CORRECTION

PATENT NO.       : 6,037,327
APPLICATION NO.  : 09/141628
DATED            : March 14, 2000
INVENTOR(S)      : Castillo et al.

Page 1 of 1

It is certified that error appears in the above-identified patent and that said Letters Patent is hereby corrected as shown below:

Please insert the following statement in Column 1, line 10:

--This invention was made with US Government support under grant number 5P50AG005136-140007 awarded by the National Institutes of Health. The US Government has certain rights in this invention.--

Signed and Sealed this

Twenty-sixth Day of August, 2008

JON W. DUDAS
*Director of the United States Patent and Trademark Office*